(12) United States Patent
Bonyuet et al.

(10) Patent No.: US 10,543,080 B2
(45) Date of Patent: *Jan. 28, 2020

(54) METHODS OF MAKING ENCAPSULATED HEART VALVES

(71) Applicant: Edwards Lifesciences Corporation, Irvine, CA (US)

(72) Inventors: Celeste C. Bonyuet, Long Beach, CA (US); Andrew L. Walls, Draper, UT (US); John F. Migliazza, Belmont Shores, CA (US); Itai Pelled, Ramat-Hasharon (IL)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/102,379

(22) Filed: Aug. 13, 2018

(65) Prior Publication Data

US 2018/0360598 A1 Dec. 20, 2018

Related U.S. Application Data

(60) Continuation of application No. 14/256,747, filed on Apr. 18, 2014, now Pat. No. 10,045,846, which is a division of application No. 13/475,210, filed on May 18, 2012, now Pat. No. 8,945,209.

(60) Provisional application No. 61/488,599, filed on May 20, 2011.

(51) Int. Cl.
*A61F 2/24* (2006.01)
*A61F 2/00* (2006.01)

(52) U.S. Cl.
CPC ............... *A61F 2/2415* (2013.01); *A61F 2/24* (2013.01); *A61F 2/2409* (2013.01); *A61F 2/2418* (2013.01); *A61F 2002/0086* (2013.01); *Y10T 29/49826* (2015.01)

(58) Field of Classification Search
CPC ....... A61F 2/24; A61F 2/2415; B29C 66/5221
See application file for complete search history.

(56) References Cited

U.S. PATENT DOCUMENTS

| | | |
|---|---|---|
| 3,143,742 A | 8/1964 | Cromie |
| 3,320,972 A | 5/1967 | High et al. |
| 3,371,352 A | 3/1968 | Siposs et al. |
| 3,546,710 A | 12/1970 | Shumakov et al. |

(Continued)

FOREIGN PATENT DOCUMENTS

| | | |
|---|---|---|
| EP | 0125393 A1 | 11/1984 |
| EP | 0143246 A2 | 6/1985 |

(Continued)

*Primary Examiner* — Christopher T Schatz
(74) *Attorney, Agent, or Firm* — Guy Cumberbatch

(57) ABSTRACT

The present disclosure concerns embodiments of implantable prosthetic devices, and in particular, implantable prosthetic valves, and methods for making such devices. In one aspect, a prosthetic device includes encapsulating layers that extend over a fabric layer and secure the fabric layer to another component of the device. In particular embodiments, the prosthetic device comprises a prosthetic heart valve, and can be configured to be implanted in any of the native heart valves. In addition, the prosthetic heart valve can be, for example, a transcatheter heart valve, a surgical heart valve, or a minimally-invasive heart valve.

20 Claims, 13 Drawing Sheets

(56) References Cited

U.S. PATENT DOCUMENTS

| | | |
|---|---|---|
| 3,574,865 A | 4/1971 | Hamaker |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,566,465 A | 1/1986 | Arhan et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,014 A | 11/1994 | Sauter et al. |
| 5,360,444 A | 11/1994 | Kusuhara |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,487,760 A | 1/1996 | Villafana |
| 5,488,789 A | 2/1996 | Religa et al. |
| 5,489,296 A | 2/1996 | Love et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,801 A | 1/1999 | Lin et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,554 A | 3/2000 | Rosenman et al. |
| 6,042,607 A | 3/2000 | Williamson, IV et al. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,264,611 B1 | 7/2001 | Ishikawa et al. |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,350,282 B1 | 2/2002 | Eberhardt |
| 6,371,983 B1 | 4/2002 | Lane |
| 6,375,620 B1 | 4/2002 | Oser et al. |
| 6,402,780 B2 | 6/2002 | Williamson, IV et al. |
| 6,409,674 B1 | 6/2002 | Brockway et al. |
| 6,425,916 B1 | 7/2002 | Garrison et al. |
| 6,440,164 B1 | 8/2002 | DiMatteo et al. |
| 6,442,413 B1 | 8/2002 | Silver |
| 6,451,047 B2 | 9/2002 | McCrea et al. |
| 6,454,799 B1 | 9/2002 | Schreck |
| 6,458,153 B1 | 10/2002 | Bailey et al. |
| 6,468,305 B1 | 10/2002 | Otte |
| 6,491,624 B1 | 12/2002 | Lotfi |
| 6,582,462 B1 | 6/2003 | Andersen et al. |
| 6,585,766 B1 | 7/2003 | Huynh et al. |
| 6,645,143 B2 | 11/2003 | VanTassel et al. |
| 6,652,464 B2 | 11/2003 | Schwartz et al. |

(56) References Cited

U.S. PATENT DOCUMENTS

| | | |
|---|---|---|
| 6,652,578 B2 | 11/2003 | Bailey et al. |
| 6,675,049 B2 | 1/2004 | Thompson et al. |
| 6,682,559 B2 | 1/2004 | Myers et al. |
| 6,685,739 B2 | 2/2004 | DiMatteo et al. |
| 6,730,118 B2 | 5/2004 | Spenser et al. |
| 6,733,525 B2 | 5/2004 | Yang et al. |
| 6,741,885 B1 | 5/2004 | Park et al. |
| 6,764,508 B1 | 7/2004 | Roehe et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,795,732 B2 | 9/2004 | Stadler et al. |
| 6,805,711 B2 | 10/2004 | Quijano et al. |
| 6,893,459 B1 | 5/2005 | Macoviak |
| 6,893,460 B2 | 5/2005 | Spenser et al. |
| 6,895,265 B2 | 5/2005 | Silver |
| 6,908,481 B2 | 6/2005 | Cribier |
| 6,939,365 B1 | 9/2005 | Fogarty et al. |
| 7,011,681 B2 | 3/2006 | Vesely |
| 7,014,653 B2 | 3/2006 | Ouriel et al. |
| 7,025,780 B2 | 4/2006 | Gabbay |
| 7,033,322 B2 | 4/2006 | Silver |
| 7,052,466 B2 | 5/2006 | Scheiner et al. |
| 7,070,616 B2 | 7/2006 | Majercak et al. |
| 7,082,330 B2 | 7/2006 | Stadler et al. |
| 7,083,640 B2 | 8/2006 | Lombardi et al. |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,416,530 B2 | 8/2008 | Turner et al. |
| 7,422,603 B2 | 9/2008 | Lane |
| 7,485,141 B2 | 2/2009 | Majercak et al. |
| 7,510,571 B2 | 3/2009 | Spiridigliozzi et al. |
| 7,513,909 B2 | 4/2009 | Lane et al. |
| 7,556,647 B2 | 7/2009 | Drews et al. |
| 7,569,072 B2 | 8/2009 | Berg et al. |
| 7,621,878 B2 | 11/2009 | Ericson et al. |
| 7,641,681 B2 | 1/2010 | Sherry et al. |
| 7,916,013 B2 | 3/2011 | Stevenson |
| 7,998,151 B2 | 8/2011 | St. Goar et al. |
| 8,066,650 B2 | 11/2011 | Lee et al. |
| 8,248,232 B2 | 8/2012 | Stevenson et al. |
| 8,253,555 B2 | 8/2012 | Stevenson et al. |
| 8,340,750 B2 | 12/2012 | Prakash et al. |
| 8,401,659 B2 | 3/2013 | Von Arx et al. |
| 8,529,474 B2 | 9/2013 | Gupta et al. |
| 8,622,936 B2 | 1/2014 | Schenberger et al. |
| 9,101,264 B2 | 8/2015 | Acquista |
| 9,101,281 B2 | 8/2015 | Reinert et al. |
| 10,045,846 B2 | 8/2018 | Bonyuet et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2001/0049555 A1 | 12/2001 | Gabbay |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0178570 A1 | 12/2002 | Sogard et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0139806 A1 | 7/2003 | Haverkost et al. |
| 2003/0149478 A1 | 8/2003 | Figulla et al. |
| 2003/0167089 A1 | 9/2003 | Lane |
| 2003/0204241 A1 | 10/2003 | Dong |
| 2003/0236568 A1 | 12/2003 | Hojeibane et al. |
| 2004/0010296 A1 | 1/2004 | Swanson et al. |
| 2004/0019374 A1 | 1/2004 | Hojeibane et al. |
| 2004/0027306 A1 | 2/2004 | Amundson et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0182511 A1 | 9/2004 | Rakos et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0047338 A1 | 3/2006 | Jenson et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |

(56) References Cited

U.S. PATENT DOCUMENTS

| | | |
|---|---|---|
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0190074 A1 | 8/2006 | Hill et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0224236 A1 | 10/2006 | Thistle |
| 2006/0241745 A1 | 10/2006 | Solem |
| 2006/0253192 A1 * | 11/2006 | Atala ............... A61F 2/2415 623/2.13 |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0118210 A1 | 5/2007 | Pinchuk |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0033543 A1 | 2/2008 | Gurskis et al. |
| 2008/0046040 A1 | 2/2008 | Denker et al. |
| 2008/0119875 A1 | 5/2008 | Ino et al. |
| 2008/0154356 A1 | 6/2008 | Obermiller et al. |
| 2008/0319543 A1 | 12/2008 | Lane |
| 2009/0036903 A1 | 2/2009 | Ino et al. |
| 2009/0076587 A1 | 3/2009 | Cully et al. |
| 2009/0192599 A1 | 7/2009 | Lane et al. |
| 2009/0209982 A1 | 8/2009 | Hoerstrup et al. |
| 2010/0036484 A1 | 2/2010 | Hariton et al. |
| 2010/0049313 A1 | 2/2010 | Alon et al. |
| 2010/0145438 A1 | 6/2010 | Barone |
| 2010/0256723 A1 | 10/2010 | Murray |
| 2012/0123284 A1 | 5/2012 | Kheradvar |
| 2012/0123529 A1 | 5/2012 | Levi et al. |
| 2012/0296382 A1 | 11/2012 | Shuros et al. |
| 2013/0144379 A1 | 6/2013 | Najafi et al. |
| 2014/0128964 A1 | 5/2014 | Delaloye |
| 2014/0188221 A1 | 7/2014 | Chung et al. |
| 2014/0364707 A1 | 12/2014 | Kintz et al. |
| 2015/0045635 A1 | 2/2015 | Tankiewicz et al. |
| 2016/0045316 A1 | 2/2016 | Braido et al. |

FOREIGN PATENT DOCUMENTS

| | | |
|---|---|---|
| SU | 1116573 A1 | 7/1985 |
| SU | 1697790 A1 | 12/1991 |
| WO | 9213502 | 8/1992 |
| WO | 9472871 | 11/1997 |
| WO | 03034950 A1 | 5/2003 |

* cited by examiner

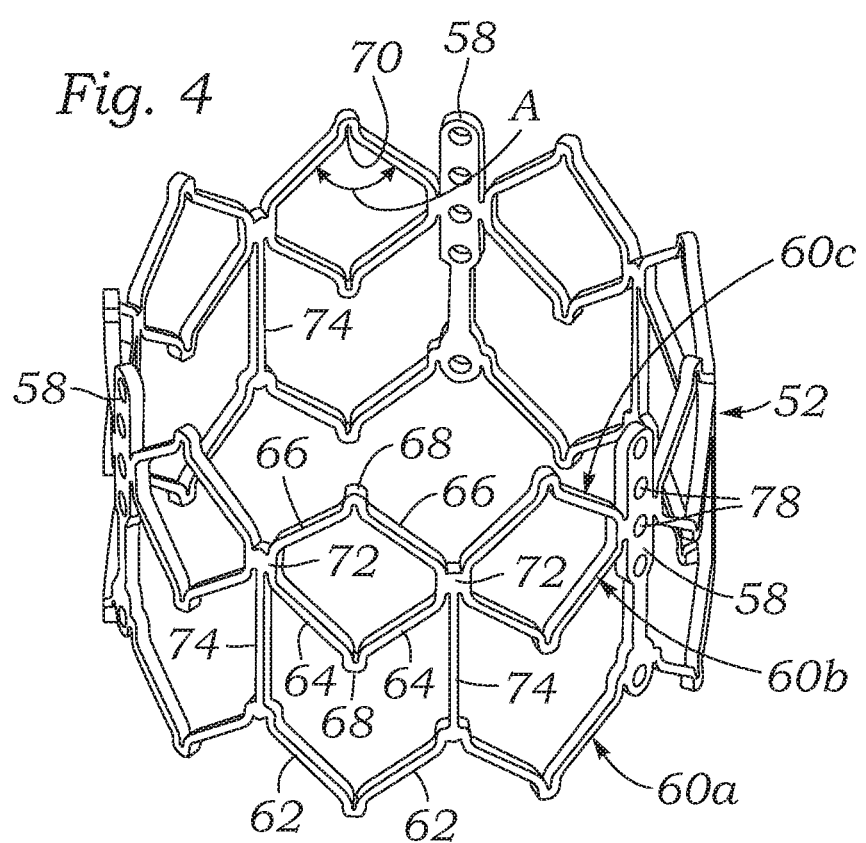

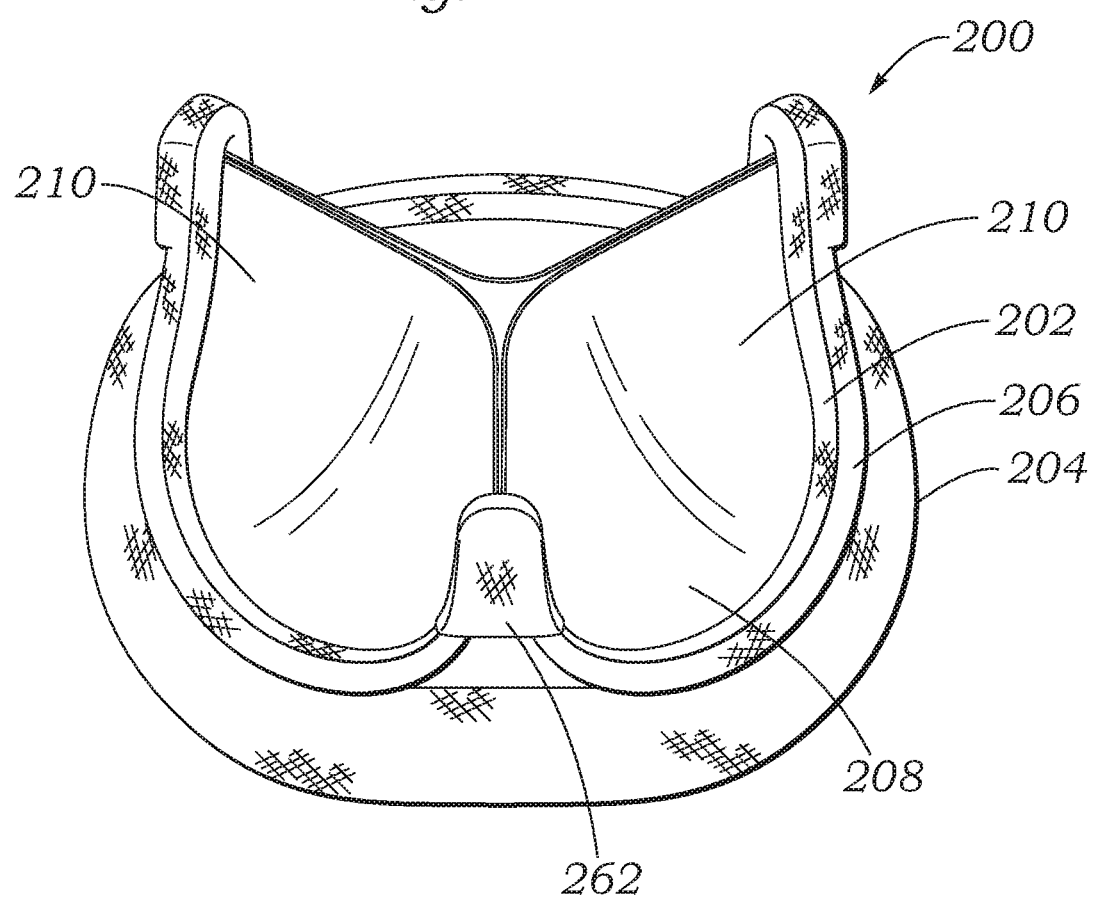

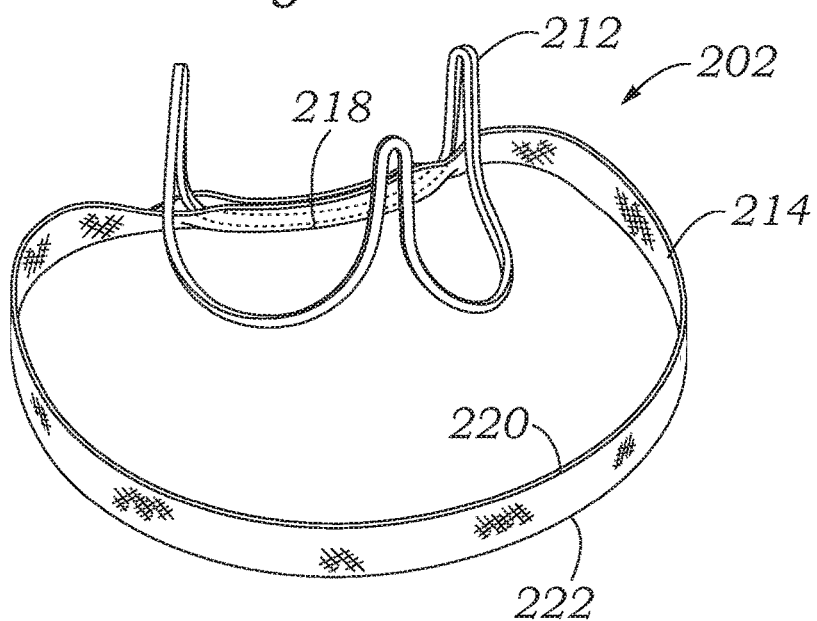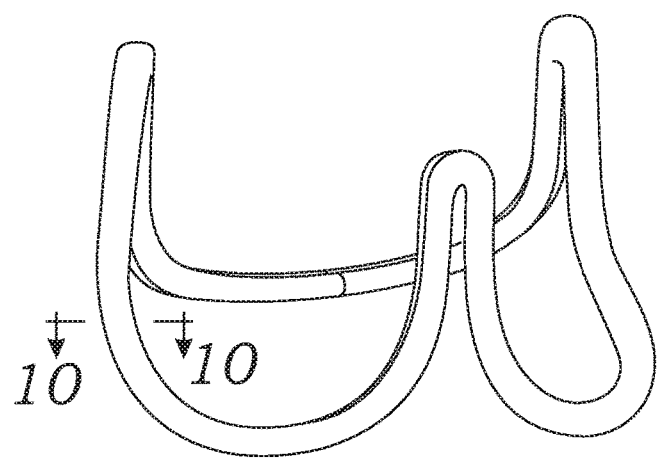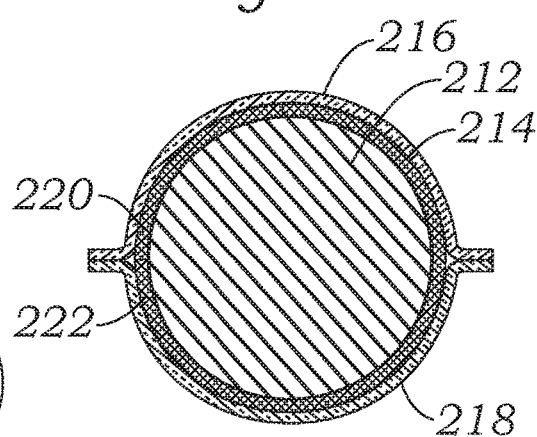

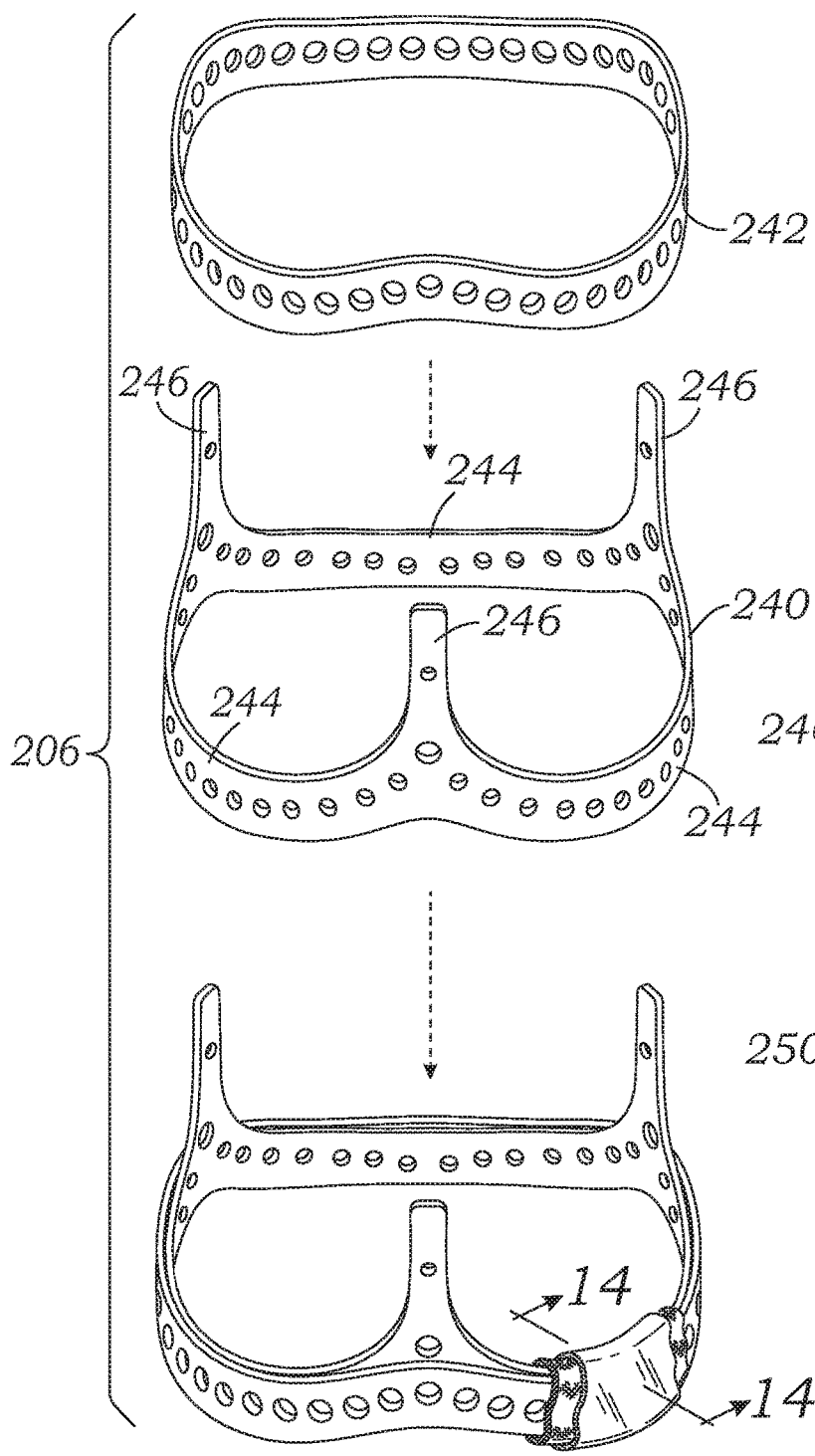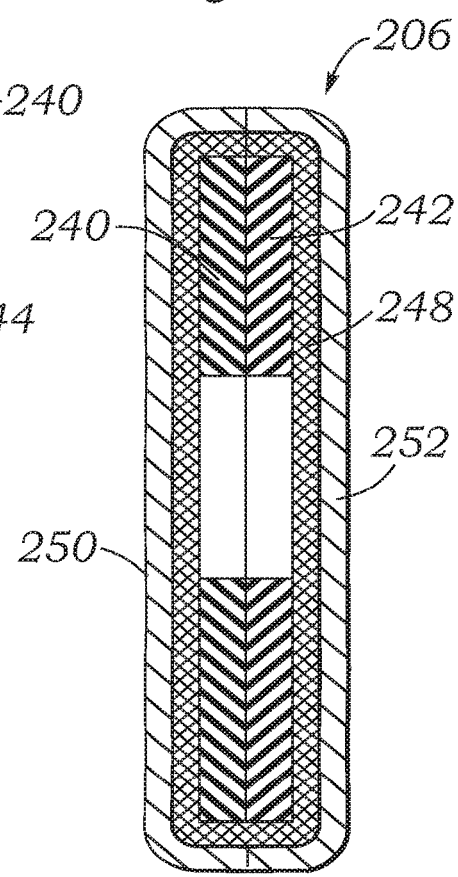

METHODS OF MAKING ENCAPSULATED HEART VALVES

RELATED APPLICATIONS

This application is a continuation of U.S. patent application Ser. No. 14/256,747, filed Apr. 18, 2014, now U.S. Pat. No. 10,045,846, which is a divisional of U.S. patent application Ser. No. 13/475,210, filed May 18, 2012, now U.S. Pat. No. 8,945,209, which claims the benefit of U.S. Patent Application No. 61/488,599, filed May 20, 2011, the entire disclosures all of which are incorporated herein.

FIELD

The present disclosure relates to implantable prosthetic devices, and more particularly, to valve prosthetics for implantation into body ducts, such as native heart valve annuluses.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Artificial or prosthetic heart valves can be classified according to the manner in which they are implanted in the body. Implantation of surgical valves requires an open-chest surgery during which the heart is stopped and the patient is placed on cardiopulmonary bypass. Transcatheter heart valves can be delivered and deployed in the body by way of catheterization without opening the chest of the patient or employing cardiopulmonary bypass. Minimally-invasive heart valves generally refer to valves that can be introduced into the body through a relatively small surgical incision yet still require the patient to be placed on cardiopulmonary bypass.

The various types of heart valves described above typically include a relatively rigid frame and a valvular structure, usually in the form of flexible valve leaflets, secured to the frame. The process for assembling a prosthetic valve is extremely labor intensive. For example, FIG. 1 illustrates a known transcatheter heart valve 10 that includes a stent, or frame, 12, a valvular structure 14 comprising three leaflets 16, and a fabric skirt 18 interposed between the frame 12 and the valvular structure 14. To assemble the valve, the skirt 18 is manually sutured to the bars of the frame using sutures 20, and then the valvular structure is sutured to the skirt and the frame. The skirt assists in anchoring the valvular structure to the frame and sealing the valve relative to the native annulus so as to prevent paravalvular leakage once implanted. As can be appreciated, the process for assembling the valve is time consuming and requires significant manual labor. Thus, it would be desirable to minimize the amount manual labor required to assemble a prosthetic valve.

SUMMARY

The present disclosure concerns embodiments of implantable prosthetic devices, and in particular, implantable prosthetic valves, and methods for making such devices. In one aspect, a prosthetic device includes encapsulating layers that extend over a fabric layer and secure the fabric layer to another component of the device. In particular embodiments, the prosthetic device comprises a prosthetic heart valve, and can be configured to be implanted in any of the native heart valves. In addition, the prosthetic heart valve can be, for example, a transcatheter heart valve, a surgical heart valve, or a minimally-invasive heart valve. The encapsulating layers desirably are formed from ePTFE or UHMWPE.

The encapsulating layers can be used to secure the fabric layer to another component of the prosthetic device without using any sutures, or substantially minimizing the number of sutures needed to secure the fabric layer in place adjacent the other component of the prosthetic device. In one example, inner and outer encapsulating layers can be used to secure a fabric skirt to the annular frame of a transcatheter heart valve, thereby replacing the need to manually sew the skirt to the frame, as currently done in the art.

This technique can also be used to secure fabric or cloth layers to various components of a surgical or minimally-invasive heart valve. For example, one or more of the sewing ring, wireform and stent assembly of a surgical or minimally-invasive heart valve typically can be covered by a cloth cover. In some valves, a single cloth cover is used to cover one or more of these components. The conventional method for assembling a cloth cover around one or more components of a surgical or minimally-invasive heart valve involves manually sewing the longitudinal edges of the cloth cover to each other to form a covering around the valve component. The disclosed technique can be used to secure a cloth covering around one or more components of a surgical or minimally-invasive heart valve in order to eliminate most or all of the manual sewing that usually is required.

In other embodiments, encapsulating layers, such as one or more layers of ePTFE or UHMWPE, can be applied to the frame of a prosthetic valve without a separate fabric layer. For example, in the case of a prosthetic valve having an expandable frame, one or more layers of ePTFE or UHMWPE can be applied to the frame (usually to the inside and outside of the frame) without a separate fabric layer to facilitate tissue in-growth and to help seal the valve against surrounding tissue.

In one representative embodiment, an implantable prosthetic valve comprises a valve component, a fabric layer disposed adjacent the valve component, and a non-absorbable encapsulating material at least partially encapsulating the fabric layer and the valve component so as to secure the fabric layer to the valve component. The encapsulating material has a porous microstructure that promotes ingrowth of surrounding tissue to assist in securing the prosthetic valve in a body lumen.

In another representative embodiment, an implantable prosthetic valve comprises a radially collapsible and expandable annular frame. The frame has an inlet end and outlet end, and a plurality of frame members defining a plurality of gaps between the frame members. The valve further comprises an annular fabric skirt positioned adjacent the frame and configured to prevent blood from flowing through gaps in the frame that are covered by the skirt. An inner tubular layer is positioned on the inside of the frame and the skirt, and an outer tubular layer is positioned on the outside of the frame and the skirt. The inner and outer layers are bonded to each other at selected areas so as to form a covering that at least partially encapsulates the frame and skirt. In addition, one or more flexible valve leaflets can be sutured to the frame and the skirt.

In another representative embodiment, a method for making an implantable prosthetic device, comprises placing a first tubular covering member on a support; placing a subassembly of the prosthetic device over the first covering member, the subassembly comprising an annular component and a fabric layer at least partially covering the annular component; placing a second tubular covering member over the subassembly; applying pressure to force the second covering member and the first covering member into contact with other; and heating the first and second covering member to form a monolithic covering that at least partially encapsulates the subassembly and thereby secures the fabric layer to the annular component.

The foregoing and other features and advantages of the invention will become more apparent from the following detailed description, which proceeds with reference to the accompanying figures.

BRIEF DESCRIPTION OF THE DRAWINGS

FIG. 4 is a perspective view of the frame of the heart valve of FIG. 2.

FIG. 7 is a perspective view of a surgical heart valve, according to another embodiment.

FIG. 8 shows the wireform of the valve of FIG. 7 and a cloth covering in the process of being wrapped around the wireform.

FIG. 9 is a perspective view of a completed cloth-covered wireform assembly of the heart valve of FIG. 7.

FIG. 10 is a cross-sectional view of the wireform assembly of FIG. 9 taken along line 10-10.

FIG. 13 includes an exploded view and an assembled view of the stent assembly of the heart valve of FIG. 7.

FIG. 14 is a cross-sectional view of the stent assembly of FIG. 13 taken along line 14-14.

DETAILED DESCRIPTION

As used in this application and in the claims, the singular forms "a," "an," and "the" include the plural forms unless the context clearly dictates otherwise. Additionally, the term "includes" means "comprises." Although the operations of exemplary embodiments of the disclosed method may be described in a particular, sequential order for convenient presentation, it should be understood that the disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed herein. Moreover, for the sake of simplicity, the attached figures may not show the various ways in which the disclosed system, method, and apparatus can be used in combination with other systems, methods, and apparatuses.

The present disclosure concerns embodiments of implantable prosthetic devices, and in particular, implantable prosthetic valves, and methods for making such devices. In one aspect, a prosthetic device includes encapsulating layers that extend over a fabric layer and secure the fabric layer to another component of the device. In particular embodiments, the prosthetic device comprises a prosthetic heart valve, and can be configured to be implanted in any of the native heart valves. In addition, the prosthetic heart valve can be, for example, a transcatheter heart valve, a surgical heart valve, or a minimally-invasive heart valve. The prosthetic valve also can comprise other types of valves implantable within other body lumens outside of the heart or heart valves that are implantable within the heart at locations other than the native valves, such as trans-atrial or trans-ventricle septum valves.

Figure 2:
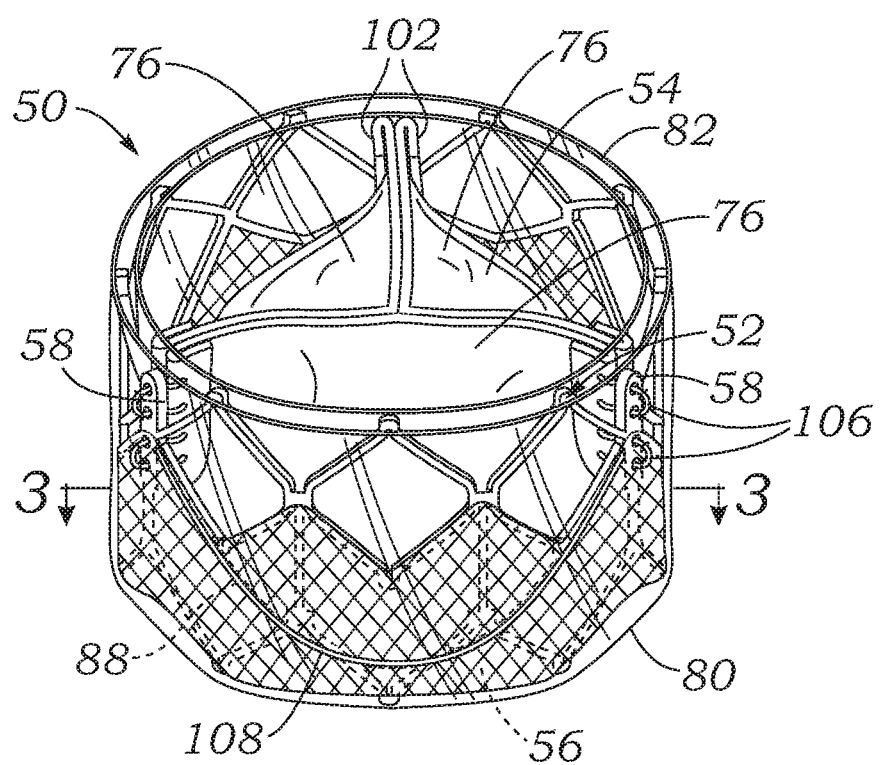
FIG. 2 is a perspective view of prosthetic transcatheter heart valve, according to one embodiment.

FIG. 2 is an example of a transcatheter heart valve 50, according to one embodiment. Valve 50 in the illustrated embodiment generally comprises a frame, or stent, 52, a leaflet structure 54 supported by the frame, and a skirt 56 secured to the outer surface of the leaflet structure. Valve 50 typically is implanted in the annulus of the native aortic valve but also can be adapted to be implanted in other native valves of the heart or in various other ducts or orifices of the body. Valve 50 has a "lower" end 80 and an "upper" end 82. In the context of the present application, the terms "lower" and "upper" are used interchangeably with the terms "inflow" and "outflow", respectively. Thus, for example, the lower end 80 of the valve is its inflow end and the upper end 82 of the valve is its outflow end.

Valve 50 and frame 52 are configured to be radially collapsible to a collapsed or crimped state for introduction into the body on a delivery catheter and radially expandable to an expanded state for implanting the valve at a desired location in the body (e.g., the native aortic valve). Frame 52 can be made of a plastically-expandable material that permits crimping of the valve to a smaller profile for delivery and expansion of the valve using an expansion device such as the balloon of a balloon catheter. Exemplary plastically-expandable materials that can be used to form the frame are described below. Alternatively, valve 50 can be a so-called self-expanding valve wherein the frame is made of a self-expanding material such as Nitinol, NiTiCo, NiTiCr, or alloys or combinations thereof. A self-expanding valve can be crimped to a smaller profile and held in the crimped state with a restraining device such as a sheath covering the valve. When the valve is positioned at or near the target site, the restraining device is removed to allow the valve to self-expand to its expanded, functional size.

Figure 1:
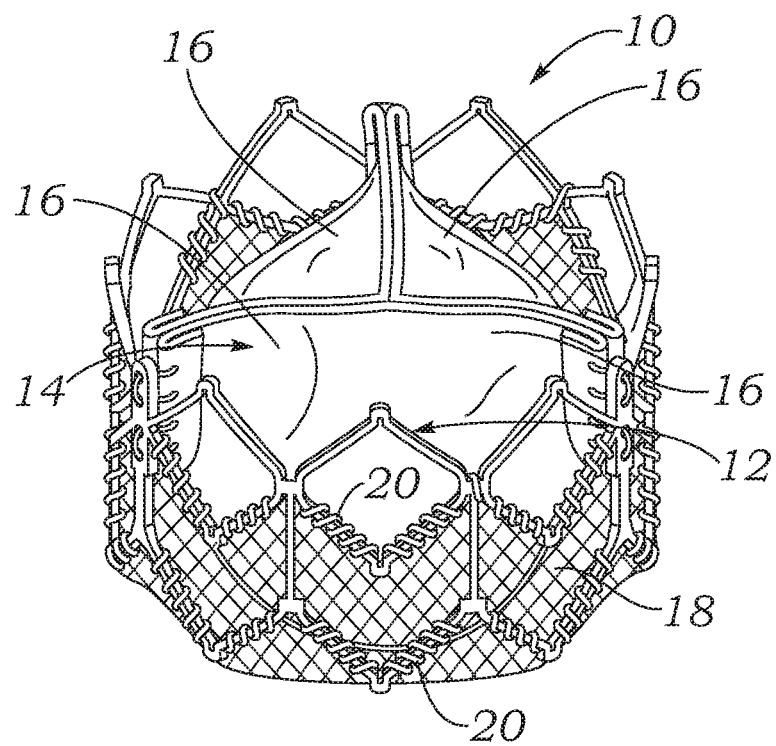
FIG. 1 is a perspective view of a prior art prosthetic transcatheter heart valve.

Referring also to FIG. 4 (which shows the frame alone for purposes of illustration), frame 52 is an annular, stent-like structure having a plurality of angularly spaced, vertically extending, commissure attachment posts, or struts, 58. Posts 58 can be interconnected via a lower row 60a of circumferentially extending struts 62 and first and second rows upper rows 60b, 60c, respectively, of circumferentially extending struts 64 and 66, respectively. The struts in each row desirably are arranged in a zig-zag or generally sawtooth like pattern extending in the direction of the circumference of the frame as shown. Adjacent struts in the same row can be interconnected to one another as shown in FIGS. 1 and 4 to form an angle A, which desirably is between about 90 and 110 degrees, with about 100 degrees being a specific example. The selection of angle A between approximately 90 and 110 degrees optimizes the radial strength of frame 52 when expanded yet still permits the frame 52 to be evenly crimped and then expanded in the manner described below.

In the illustrated embodiment, pairs of adjacent circumferential struts in the same row are connected to each other by a respective, generally U-shaped crown structure, or crown portion, 68. Crown structures 68 each include a horizontal portion extending between and connecting the adjacent ends of the struts such that a gap 70 is defined between the adjacent ends and the crown structure connects the adjacent ends at a location offset from the strut's natural point of intersection. Crown structures 68 significantly reduce residual strains on the frame 52 at the location of struts 62, 64, 66 during crimping and expanding of the frame 52 in the manner described below. Each pair of struts 64 connected at a common crown structure 68 forms a cell with an adjacent pair of struts 66 in the row above. Each cell can be connected to an adjacent cell at a node 72. Each node 72 can be interconnected with the lower row of struts by a respective vertical (axial) strut 74 that is connected to and extends between a respective node 72 and a location on the lower row of struts 62 where two struts are connected at their ends opposite crown structures 68.

In certain embodiments, lower struts 62 have a greater thickness or diameter than upper struts 64, 66. In one implementation, for example, lower struts 62 have a thickness of about 0.42 mm and upper struts 64, 66 have a thickness of about 0.38 mm. Because there is only one row of lower struts 62 and two rows of upper struts 64, 66 in the illustrated configuration, enlargement of lower struts 62 with respect to upper struts 64, 66 enhances the radial strength of the frame at the lower area of the frame and allows for more uniform expansion of the frame.

Suitable plastically-expandable materials that can be used to form the frame include, without limitation, stainless steel, cobalt, chromium, titanium, nickel, or alloys or combinations thereof (e.g., a nickel-cobalt-chromium alloy). Some embodiments can comprise a flexible biocompatible polymer, such as polypropylene, polyurethanes or silicon. In particular embodiments, frame 52 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 52 provides superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

Leaflet structure 54 can comprise three leaflets 76, which can be arranged to collapse in a tricuspid arrangement, as best shown in FIG. 2. Lower edge 88 of leaflet structure 54 desirably has an undulating, curved scalloped shape. By forming the leaflets with this scalloped geometry, stresses on the leaflets are reduced, which in turn improves durability of the valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the valve. The leaflets 76 can be formed of bovine pericardial tissue, biocompatible synthetic materials, or various other suitable natural or synthetic materials as known in the art and described in U.S. Pat. No. 6,730,118, which is incorporated by reference herein.

Figure 3:
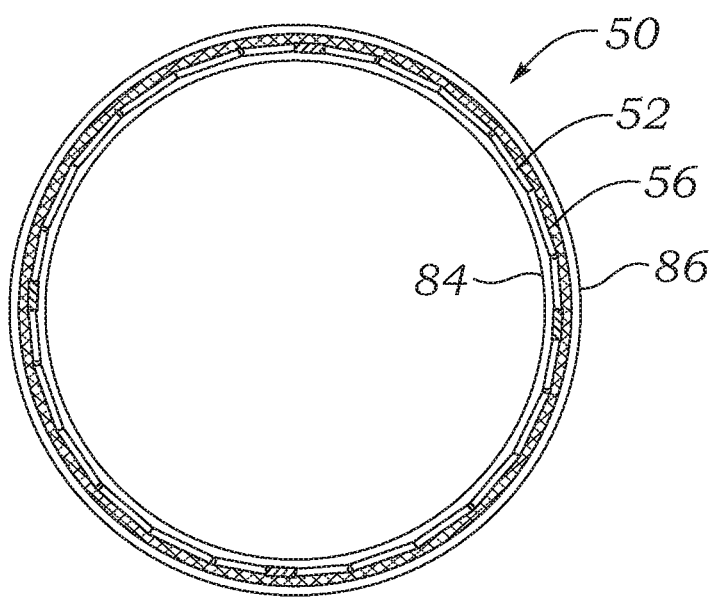
FIG. 3 is a cross-section view of the heart valve of FIG. 2 taken along line 3-3.

The skirt 56 can be formed, for example, of polyethylene terephthalate (PET) ribbon or polyester fabric (e.g., Dacron). The thickness of the skirt can vary, but is desirably less than 6 mil, and desirably less than 4 mil, and even more desirably about 2 mil. Traditionally, fabric skirts have been secured to frames using sutures, as illustrated in FIG. 1. In contrast, in the illustrated embodiment, skirt 56 desirably is secured to frame 52 without sutures and instead is secured to frame 52 with inner and outer encapsulating layers 84, and 86, respectively (FIG. 3). The encapsulating layers 84, 86 are fused, bonded, or otherwise secured to each other through the openings in the frame 52, which effectively encapsulates the frame 52 and the skirt 56 to secure these components in their assembled state shown in FIG. 2.

The skirt 56 of the prosthetic valve can serve several functions. In particular embodiments, for example, the skirt primarily functions to anchor the leaflet structure to the frame. In addition, the skirt 56, in cooperation with the encapsulating layers 84, 86, help prevent (or decrease) perivalvular leakage.

In the illustrated embodiment, each of the inner and outer layers 84, 86 extend the axial length of the frame 52 (from the lower end 80 to the upper end 82), and therefore completely encapsulates or substantially encapsulates the entire frame 52 and skirt 56. In alternative embodiments, the layers 84, 86 can be shorter than the axial length of the frame 52 and/or the skirt 56 such that the layers 84, 86 only encapsulate selected portions of the frame and the skirt. Although in the illustrated embodiment the layers 84, 86 are tubular or cylindrical in shape, the inner and outer layers 84, 86 need not extend along the inner and outer surfaces of the frame in the circumferential direction through 360 degrees. In other words, the inner and outer layers 84, 86 can have a cross-sectional profile (in a plane perpendicular to the axis of the lumen of the valve) that is not a complete circle.

The encapsulating layers 84, 86 desirably are made of a non-absorbable polymeric material (i.e., a material that does not dissolve once implanted in the body). Examples of such materials include without limitation, expanded polytetrafluoroethylene (ePTFE), unexpanded porous PTFE, woven polyester or expanded PTFE yarns, PTFE, ultrahigh molecular weight polyethylene (UHMWPE), other polyolefins, composite materials such as ePTFE with PTFE fibers, or UHMWPE film with embedded UHMWPE fibers, polyimides, silicones, polyurethane, hydrogels, fluoroethylpolypropylene (FEP), polypropylfluorinated amines (PFA), other related fluorinated polymers, or various combinations of any of these materials. In particular embodiments, the encapsulating layers 84, 86 are formed from respective tubes made of a suitable polymeric material (e.g., ePTFE tubes or UHMWPE tubes) that are bonded to each other when subjected to heat treatment, as described in detail below.

Microporous expanded polytetrafluoroethylene (ePTFE) tubes can be made by of a number of well-known methods. Expanded PTFE is frequently produced by admixing particulate dry polytetrafluoroethylene resin with a liquid lubricant to form a viscous slurry. The mixture can be poured into a mold, typically a cylindrical mold, and compressed to form a cylindrical billet. The billet can then be ram extruded through an extrusion die into either tubular or sheet structures, termed extrudates in the art. The extrudates comprise an extruded PTFE-lubricant mixture called "wet PTFE." Wet PTFE has a microstructure of coalesced, coherent PTFE resin particles in a highly crystalline state. Following extrusion, the wet PTFE can be heated to a temperature below the flash point of the lubricant to volatilize a major fraction of the lubricant from the PTFE extrudate. The resulting PTFE extrudate without a major fraction of lubricant is known in the art as dried PTFE. The dried PTFE can then be either uniaxially, biaxially or radially expanded using appropriate mechanical apparatus known in the art. Expansion is typically carried out at an elevated temperature, e.g., above room temperature but below 327 degrees C., the crystalline melt point of PTFE. Uniaxial, biaxial or radial expansion of the dried PTFE causes the coalesced, coherent PTFE resin to form fibrils emanating from nodes (regions of coalesced PTFE), with the fibrils oriented parallel to the axis of expansion. Once expanded, the dried PTFE is referred to as expanded PTFE ("ePTFE") or microporous PTFE.

UHMWPE is made up of very long chains of polyethylene, with molecular weight numbering in the millions, usually between 2 and 6 million. It is highly resistant to corrosive chemicals, has extremely low moisture absorption and a very low coefficient of friction. It is self-lubricating and highly resistant to abrasion. UHMWPE is processed using compression molding, ram extrusion, gel spinning, and sintering. UHMWPE is available commercially as a powder, in sheets or rods, and as fibers.

Referring now to FIGS. 5A-5D and 6, an exemplary method for forming the valve 50 will now be described. Although the use of ePTFE is described below, it is merely exemplary in nature and is not intended as a limitation. It is to be understood that other materials such as UHMWPE, composite materials, or any other non-absorbable polymeric material described above can be used.

Figure 5A:
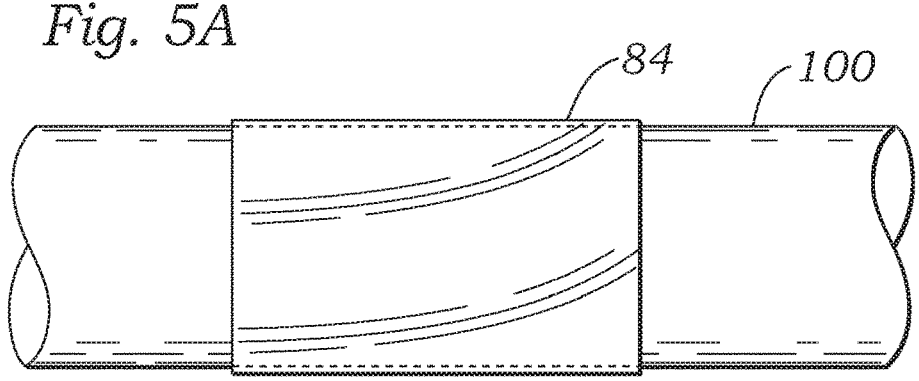
FIGS. 5A-5D illustrates a method for securing a fabric skirt to the frame of a heart valve by encapsulating the skirt and the frame.
Figure 5B:
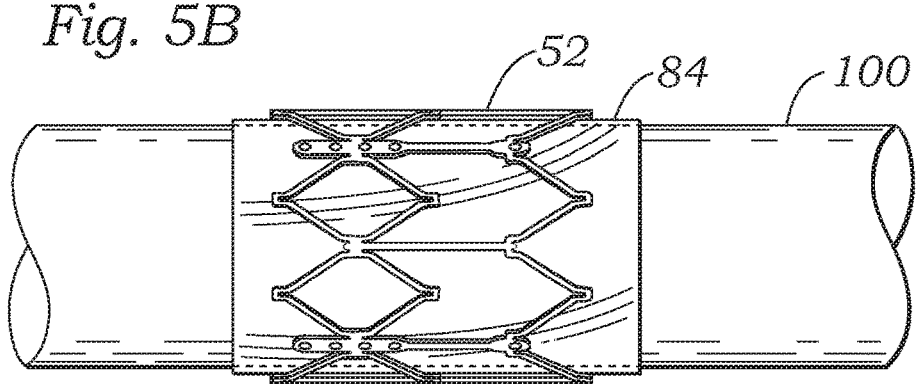
Figure 5C:
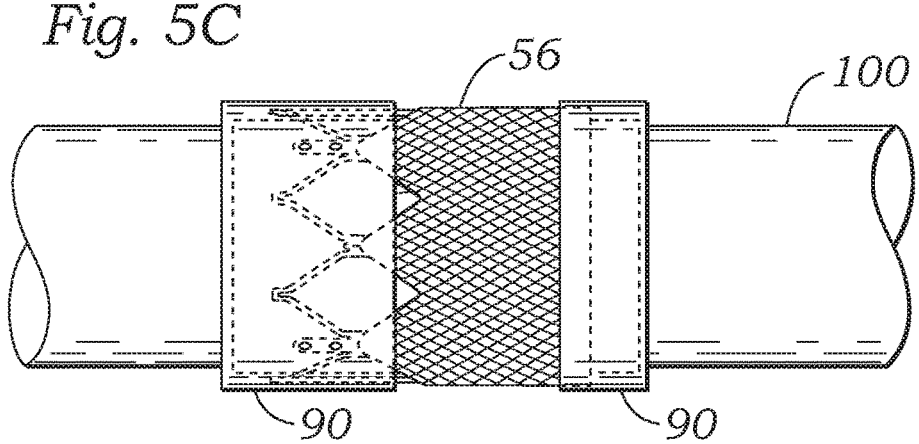
Figure 5D:
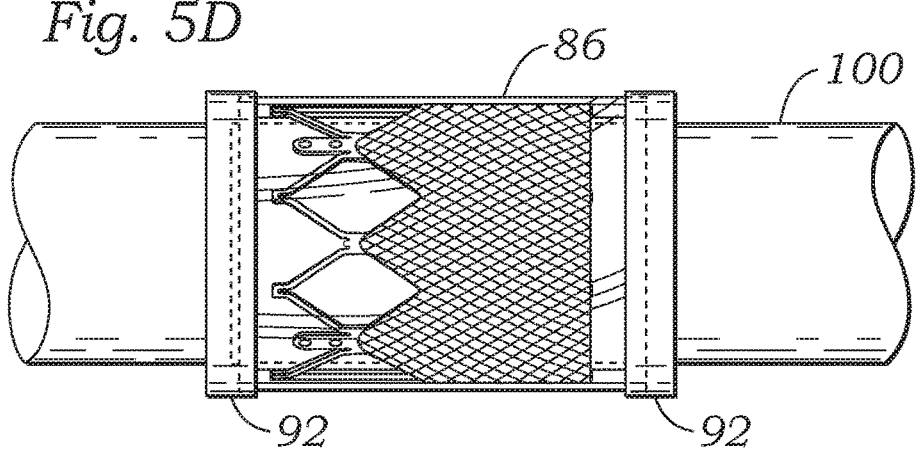
Figure 6:
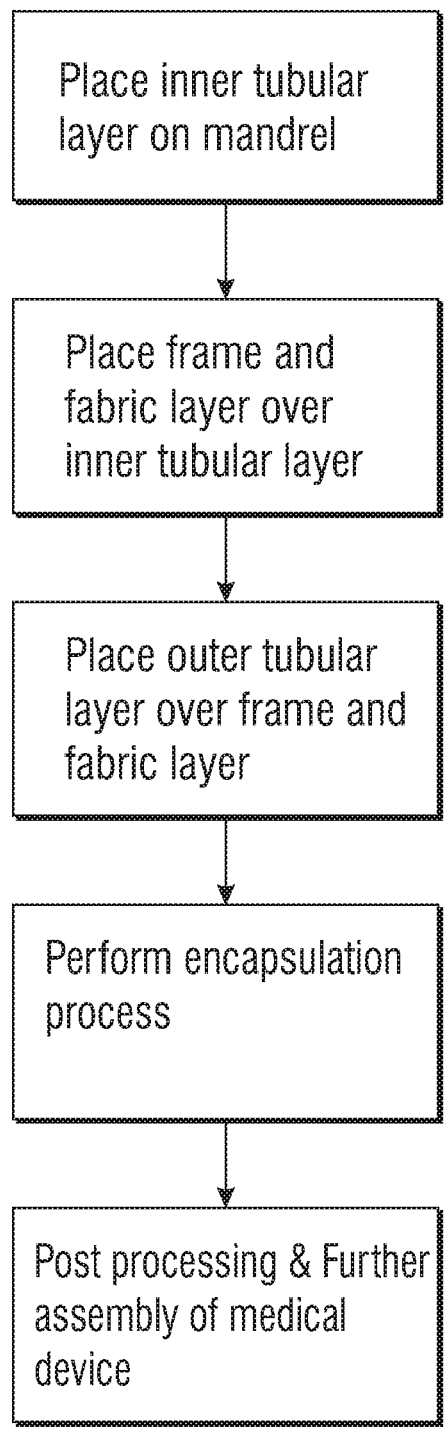
FIG. 6 is a flow chart illustrating a method of constructing the heart valve shown in FIG. 2, according to one embodiment.

First, as depicted in FIG. 5A, an inner layer 84 comprising an ePTFE tube can be placed on a mandrel 100. Second, as depicted in FIG. 5B, a frame 52 can be placed over the inner layer 84. Third, as depicted in FIG. 5C, the skirt 56 can be placed over the frame 52. The skirt 56 can be in the form of a sheet of material that is tightly wrapped around the outer surface of the frame. Layers of PTFE tape 90 can be wrapped around the opposite ends of the skirt and the frame to temporarily secure the location and placement of the skirt on the frame. Fourth, as depicted in FIG. 5D, an outer layer 86 comprising an ePTFE tube can be placed over the skirt 56. After the outer layer is in position, the temporary tape layers 90 can be removed. The tape layers 90 help maintain the location of the skirt relative to the frame and the location of the skirt and the frame relative to the mandrel as the outer layer 86 is slid over the mandrel and over the skirt and the frame. As further shown in FIG. 5D, further layers of PTFE tape 92 can now be wrapped around the ends of the outer layer 86 to help secure the position of the outer layer to the underlying layers of the assembly and to the mandrel during subsequent processing.

An alternative way to encapsulate the frame with polymer is by using the electrospinning technique. Electrospinning uses an electrical charge to draw very fine (typically on the micro or nano scale) fibers from a liquid.

The assembly shown in FIG. 5D can now undergo an encapsulation process whereby the assembly is subjected to heat and/or pressure to cause the inner and outer layers to bond to each other through the openings in the frame 52 and at the ends of the tubular layers that extend beyond the opposite ends of the frame 52 to encapsulate the frame and the skirt between the inner and outer layers. During this step, the entire outer surface of the assembly on the mandrel can be tightly wrapped with a suitable material (e.g., PTFE tape) to apply pressure to the various layers of the assembly. The entire assembly, including the mandrel, can be transferred to an oven where the inner and outer layers 84, 86 are sintered by being heated to a predetermined temperature. In one implementation, for example, the inner and outer layers are sintered by being heated to a temperature above 327 degrees C., the crystalline melt point of PTFE.

During the sintering process the ePTFE is restrained against uniaxial, biaxial or radial contraction. Sintering causes at least a portion of the crystalline PTFE to change from a crystalline state to an amorphous state. The conversion from a highly crystalline structure to one having an increased amorphous content locks the node and fibril microstructure, as well as its orientation relative to the axis of expansion, and provides a dimensionally stable tubular or sheet material upon cooling.

After the sintering process, the assembly is removed from the oven and allowed to cool. The material wrapped around the assembly, as well as tape layers 92, can now be removed. The portions of the inner and outer layers 84, 86 that extend beyond the opposite ends of the stent 52 can be trimmed so that the inner and outer layers 84, 86 are the same length or substantially the same length as the frame 52. In this manner, the frame 52 can be completely covered or substantially covered by layers 84, 86. If desired, selected portions of the inner and outer layers 84, 86 can be removed to facilitate crimping of the valve for delivery into a patient. Suitable techniques and mechanisms can be used to selectively remove portions of layers 84, 86, such as laser cutting. For example, portions of the inner and outer layers 84, 86 that cover the openings in the frame 52 can be cut or otherwise removed to minimize the amount of material in the valve, which can facilitate crimping of the valve to a relatively small diameter. In particular embodiments, the portions of layers 84, 86 extending from the upper edge of the skirt 56 to the upper edge of the frame can be completely removed to expose the struts of the frame that extend above the upper edge of the skirt.

In an alternative embodiment, the skirt 56 can be preformed in a tubular or cylindrical configuration. In this embodiment, the skirt can be positioned on the frame 52 by first partially crimping the frame to a diameter smaller than the diameter of the skirt. The skirt is then placed over the partially crimped frame and then the frame is expanded back to its functional size. The skirt desirably is sized such that the expanded frame applies at least some outward radial pressure against the skirt to assist in retaining the skirt on the frame. The frame and skirt assembly can then be loaded onto inner layer 84 (already on the mandrel), and encapsulated following the process described above. In another embodiment, the skirt 56 can be placed on the inside of the frame 52. For example, the skirt 56 can be in the form of a sheet of material that is wrapped around inner layer 84 prior to placing the frame on the mandrel, or it can have a tubular configuration that is slid onto inner layer 84 prior to placing the frame on the mandrel.

Leaflet structure 54 can be attached to the skirt 56 and/or the frame 52 using sutures or other suitable techniques or mechanisms. In the illustrated embodiment shown in FIG. 2, for example, each leaflet 76 has a tab 102 that is sutured to an adjacent tab of another leaflet to form a commissure of the leaflet structure. Each commissure can be secured to a commissure post 58 of the frame 52, such as with sutures 106 that extend through the leaflet tabs 102 and apertures in the commissure posts 58 of the frame. The lower, or inflow, end portion of the leaflets 76 can be sutured directly to the skirt 56 along a suture line 108 that tracks the curvature of the scalloped lower edge 88 of the leaflet structure. Any suitable suture, such as an Ethibond suture, can be used to secure the leaflets to the skirt along suture line 108.

In certain embodiments, the lower edges of the leaflets can be secured to the skirt 56 via a thin PET reinforcing strip (not shown), as disclosed in U.S. Pat. No. 7,993,394, which is incorporated herein by reference. As described in U.S. Pat. No. 7,993,394, the reinforcing strip can be sutured to the lower edges of the leaflets. The reinforcing strip and the lower edges of the leaflets can then be sutured to the skirt 56 along suture line 108. The reinforcing strip desirably is secured to the inner surfaces of the leaflets 76 such that the lower edges of the leaflets become sandwiched between the reinforcing strip and the skirt 56 when the leaflets and the reinforcing strip are secured to the skirt. The reinforcing strip enables a secure suturing and protects the pericardial tissue of the leaflet structure from tears.

As noted above, the conventional method for securing a skirt to a frame involves manually suturing the skirt to the frame. In contrast, the illustrated embodiment relies on the inner and outer layers 84, 86 to secure the skirt 56 in place relative to the frame. As can be appreciated, this technique for securing the skirt to the frame can significantly reduce the amount of labor required to assemble a valve. The use of layers 84, 86 provides other advantages as well. For example, the outer layer 86, when formed from ePTFE or UHMWPE, has a porous microstructure that facilitates tissue in-growth from surrounding tissue after the valve is implanted.

In addition, inner and outer layers 84, 86 can protect the leaflets 76 during crimping and facilitate even and predictable crimping of the valve. When a prosthetic valve is placed in a crimping apparatus to radial compress the valve to a smaller diameter for insertion into a patient, the leaflets of the valve are pressed against the inner surface of the metal frame and portions of the tissue can protrude into the open cells of the frame between the struts and can be pinched due to the scissor-like motion of the struts of the frame. If the valve is severely crimped to achieve a small crimping size, this scissor-like motion can result in cuts and rupture of the tissue leaflets. To protect the leaflets during crimping, it is known to place a deformable material around the valve to prevent direct contact between the hard surface of the jaws of the crimping apparatus and the valve. The deformable material can protrude into the open cells, thereby preventing the leaflets from entering this space and being pinched by metal struts of the frame. Layers 84, 86 function in a manner similar to this deformable material to protect leaflets from being pinched during crimping. As such, the disclosed valve 50 can be placed in a crimping apparatus without an additional protective layer of material surrounding the valve. Due to the presence of layers 84, 86, the valve 50 can be crimped onto the balloon of a balloon catheter in an even and predictable manner that forms a very ordered structure of balloon-leaflets-frame (from inward to outward). Additionally, inner layer 84 can prevent direct contact between the leaflets 76 and the frame during working cycles of the valve (i.e., as the valve leaflets open and close in response to blood pressure) to protect the leaflets against damage caused by contact with the frame.

Moreover, as noted above, the skirt 56 can be a fabric, such as a PET cloth. PET or other fabrics are substantially non-elastic (i.e., substantially non-stretchable and non-compressible). As such, in known prosthetic valves, the skirt can wrinkle after expansion from the crimped diameter. In the illustrated embodiment, the skirt 56 can be tightly compressed against the frame by layers 84, 86 such that when the valve is expanded to its functional size from the crimped state, the skirt can recover to its original, smooth surfaces with little or no wrinkling.

The encapsulation process described above in the context of securing a skirt to the frame of an expandable transcatheter heart valve. The skirt typically is more durable than the ePTFE layers and therefore the skirt reinforces the ePTFE layers where they undergo stresses from cyclic loading of the valve. However, in alternative embodiments, the valve can be formed without the skirt 56 to permit crimping of the valve to a smaller delivery diameter. In such embodiments, the ePTFE layers 84, 86 serve as the primary sealing mechanism that prevents paravalvular leakage through the frame of the valve. In other embodiments, the skirt 56 can be used to reinforce only selected portions of the layers 84, 86, such as those portions of layers 84, 86 subject to greatest loading, while the remaining portions of layers 84, 86 do not contain a fabric layer or skirt.

It should be noted that the encapsulation process can be utilized to secure a fabric or woven textile element to other components of a prosthetic valve. For example, surgical valves (valves which are typically implanted via open-heart surgery) include several components that are covered with a cloth or fabric material. Known surgical valves typically have a sewing ring and one or more stent components, each of which are covered with a cloth member. The cloth member typically is wrapped around the valve component and the longitudinal edges of the cloth member are manually stitched to each other to secure the cloth member around the valve component. As can be appreciated, this is a tedious and time-consuming process.

Figure 11:
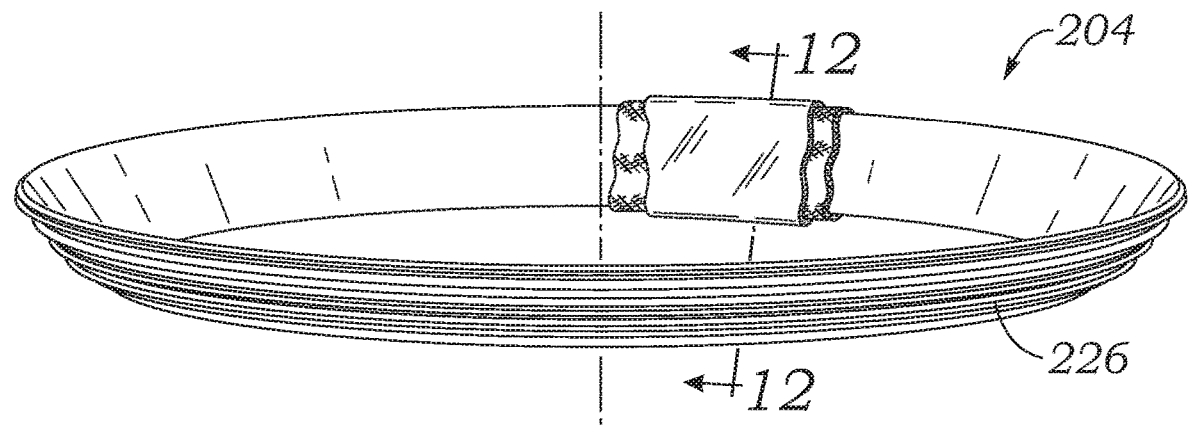
FIG. 11 is a perspective view of a cloth-covered sewing ring assembly of the heart valve of FIG. 7.
Figure 12:
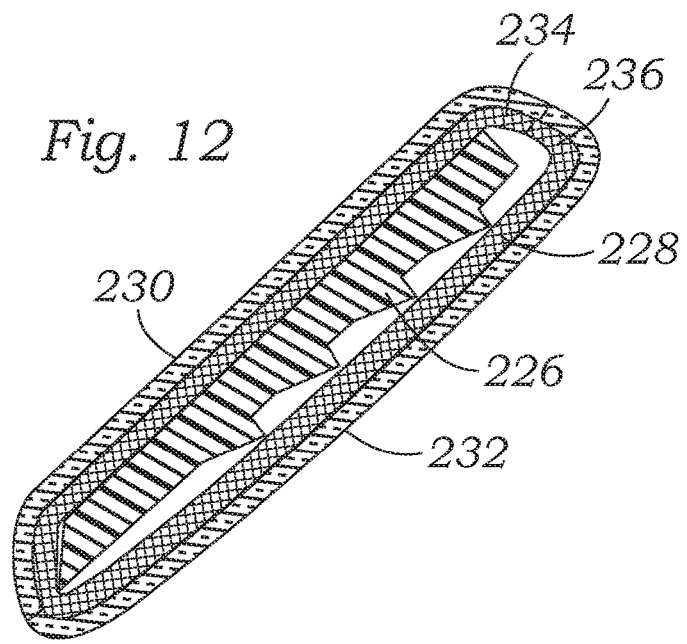
FIG. 12 is a cross-sectional view of the sewing ring assembly of FIG. 11 taken along line 12-12.
Figure 15:
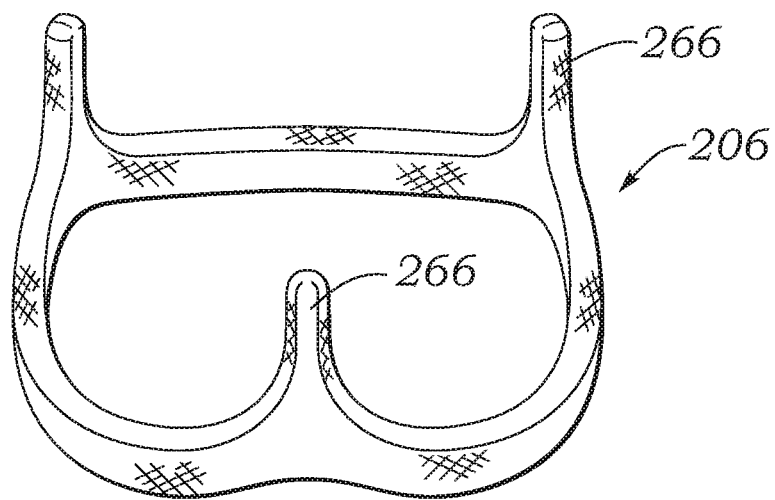
FIG. 15 is a perspective view of the stent assembly.

Accordingly, another embodiment of the present disclosure utilizes the encapsulation process described herein to secure cloth members around components of a surgical valve to reduce the amount of the manual labor required to assemble the valve. FIG. 7 shows a surgical valve 200, according to one embodiment, that includes multiple components that are formed by the encapsulation process. The valve 200 generally includes a wireform assembly 202 (as best shown in FIGS. 8-10), a sewing ring assembly 204 (as best shown in FIGS. 11-12), a stent assembly 206 (as best shown in FIGS. 13-15), and a valvular structure 208 (as best shown in FIG. 7). The valvular structure 208 can comprises three leaflets 210 arranged in a tricuspid arrangement as known in the art.

Referring to FIGS. 8-10, the wireform assembly 202 comprises a wireform 212, a cloth cover 214 and encapsulating layers 216, 218. As used herein, the term "wireform" refers generally to a portion of a prosthetic heart valve that provides support for the leaflets of the valve. The wireform typically is formed from one or more pieces of wire but also can be formed from other similarly-shaped elongate members. The wireform can also be cut or otherwise formed from tubing or a sheet of material. The wireform can have any of various cross sectional shapes, such as a square, rectangular, or circle (as shown in FIG. 10), or combinations thereof. In particular embodiments, the wireform 212 is made of a relatively rigid metal, such as stainless steel or Elgiloy (a Co—Cr—Ni alloy).

FIG. 8 shows the wireform 212 partially covered by the cloth cover 214. The cloth cover can be formed of any biocompatible fabric, such as, for example, polyethylene terephthalate. The cloth cover 214 comprises an elongated strip of material having opposing ends that are brought together to form a butt joint in the manner shown in FIG. 8. The opposing longitudinal edges 220, 222 of the cloth cover are then wrapped around the wireform 212. It is known to stitch together the longitudinal edges of the cloth covering along its entire length, which is time-consuming process. Instead, in the illustrated embodiment, the cloth cover is secured around the wireform 212 by the encapsulating layers 216, 218.

The encapsulating layers can be formed in a process similar to that described above for securing encapsulating layers 84, 86 around frame 52 and skirt 56. In one specific approach, for example, a first ePTFE tube, which forms layer 216, can be placed on a mandrel. The first ePTFE tube can have a diameter that is slightly smaller than the diameter of the wireform 212 and an axial length that is slightly greater than the axial length of the wireform 212. The cloth covered wireform can then be placed over the first ePTFE tube. A second ePTFE tube, which forms layer 218 is then placed over the cloth covered wireform. The second ePTFE tube can have a diameter and axial length that are slightly greater than that of the wireform 212. To help retain the cloth cover 214 wrapped around the wireform 212 during the previous steps, the longitudinal edges 220, 222 can be stitched together at a few selected locations along the length of the cloth cover. The entire assembly can then be wrapped with a suitable material and then placed in an oven to sinter the ePTFE tubes. After sintering, the wrapping material is removed. The first and second ePTFE tubes can have a length that is slightly greater than the axial length of the wireform. In this manner, the entire assembly forms a tubular body completely encapsulating the wireform. Excess ePTFE material can be cut away to form layers 216, 218 that together form a covering that closely conforms to the shape of the wireform 212, as depicted in FIG. 10.

Referring to FIGS. 11 and 12, the sewing ring assembly 204 comprises a sewing ring insert 226, a cloth cover 228, and encapsulating layers 230, 232. The sewing ring insert 226 can have a conventional construction and can be made of a suture permeable material for suturing the valve to a native annulus, as known in the art. For example, the sewing ring insert 226 can be made of a silicone-based material, although other suture-permeable materials can be used. The cloth cover 228 can be formed of any biocompatible fabric, such as, for example, polyethylene terephthalate. As with the wireform assembly, it is known to stitch together the edges of the cloth covering of the sewing ring along its length, which is a time-consuming process. Instead, in the illustrated embodiment, the cloth covering 228 can be secured around the sewing ring insert by the encapsulating layers 230, 232.

The encapsulating layers can be formed in a process similar to that described above for securing encapsulating layers 84, 86 around frame 52 and skirt 56. In one specific approach, for example, a first ePTFE tube, which forms layer 230, can be placed on a mandrel. The first ePTFE tube can have a diameter that is slightly smaller than the diameter of the sewing ring insert 226 and an axial length that is slightly greater than the axial length of the sewing ring insert. The cloth covered sewing ring insert can then be placed over the first ePTFE tube. The mandrel can have a tapered or substantially conical surface portion that is shaped to support the sewing insert. A second ePTFE tube, which forms layer 232 is then placed over the cloth covered sewing ring insert. The second ePTFE tube can have a diameter and axial length that are slightly greater than that of the sewing ring insert. To help retain the cloth cover 228 wrapped around the sewing ring insert during the previous steps, the longitudinal edges 234, 236 can be stitched together at a few selected locations along the length of the cloth cover. The entire assembly can then be wrapped with a suitable material and then placed in an oven to sinter the ePTFE tubes. After sintering, the wrapping material is removed. The first and second ePTFE tubes can have a length that is slightly greater than the axial length of the sewing ring assembly. In this manner, the entire assembly forms an annular body completely encapsulating the sewing ring and cloth cover. Excess ePTFE material can be cut away to form layers 230, 232 that together form a covering that closely conforms to the shape of the sewing ring insert, as depicted in FIG. 12.

Referring to FIGS. 13 and 14, the stent, or band, assembly 206 can comprise an inner support 240 and an outer band 242 disposed around the inner support 240. The inner support 240 can comprise cusp portions 244 extending between upstanding commissure portions 246. The outer band 242 can be shaped to conform to the curvature of the cusp portions of the inner support. The inner support 240 desirably is made of a polymeric material, such as polyester, although materials, including metals and other polymeric materials can be used. The outer band desirably is made of a relatively rigid metal, such as Elgiloy (a Co—Cr—Ni alloy) or stainless steel. As best shown in FIG. 14, a cloth cover 248 in the illustrated embodiment completely covers the inner support 240 and the outer band 242. Encapsulating layers 250, 252 encapsulate the cloth cover 248. As with the wireform assembly, it is known to stitch together the edges of the cloth covering of the stent assembly along its length, which is a time-consuming process. Instead, in the illustrated embodiment, the cloth covering 248 can be secured around the inner support and outer band by the encapsulating layers 250, 252.

The encapsulating layers can be formed in a process similar to that described above for securing encapsulating layers 84, 86 around frame 52 and skirt 56. In one specific approach, for example, a first ePTFE tube, which forms layer 250, can be placed on a mandrel. The first ePTFE tube can have a diameter that is slightly smaller than the diameter of the inner support 240 and an axial length that is slightly greater than the axial length of the inner support 240. The cloth covered stent assembly (i.e., the inner support 240, outer band 242, and cloth cover 248) can then be placed over the first ePTFE tube. A second ePTFE tube, which forms layer 252 is then placed over the cloth covered wireform. The second ePTFE tube can have a diameter and axial length that are slightly greater than that of the inner support 240. To help retain the cloth cover 248 wrapped around the inner support 240 and the outer band 242 during the previous steps, the longitudinal edges 254, 256 can be stitched together at a few selected locations along the length of the cloth cover. The entire assembly can then be wrapped with a suitable material and then placed in an oven to sinter the ePTFE tubes. After sintering, the wrapping material is removed. The first and second ePTFE tubes can have a length that is slightly greater than the axial length of the wireform. In this manner, the entire assembly forms a tubular body completely encapsulating the wireform. Excess ePTFE material can be cut away to form layers 250, 252 that together form a covering that closely conforms to the shape of the cloth covered stent assembly.

Figure 16:
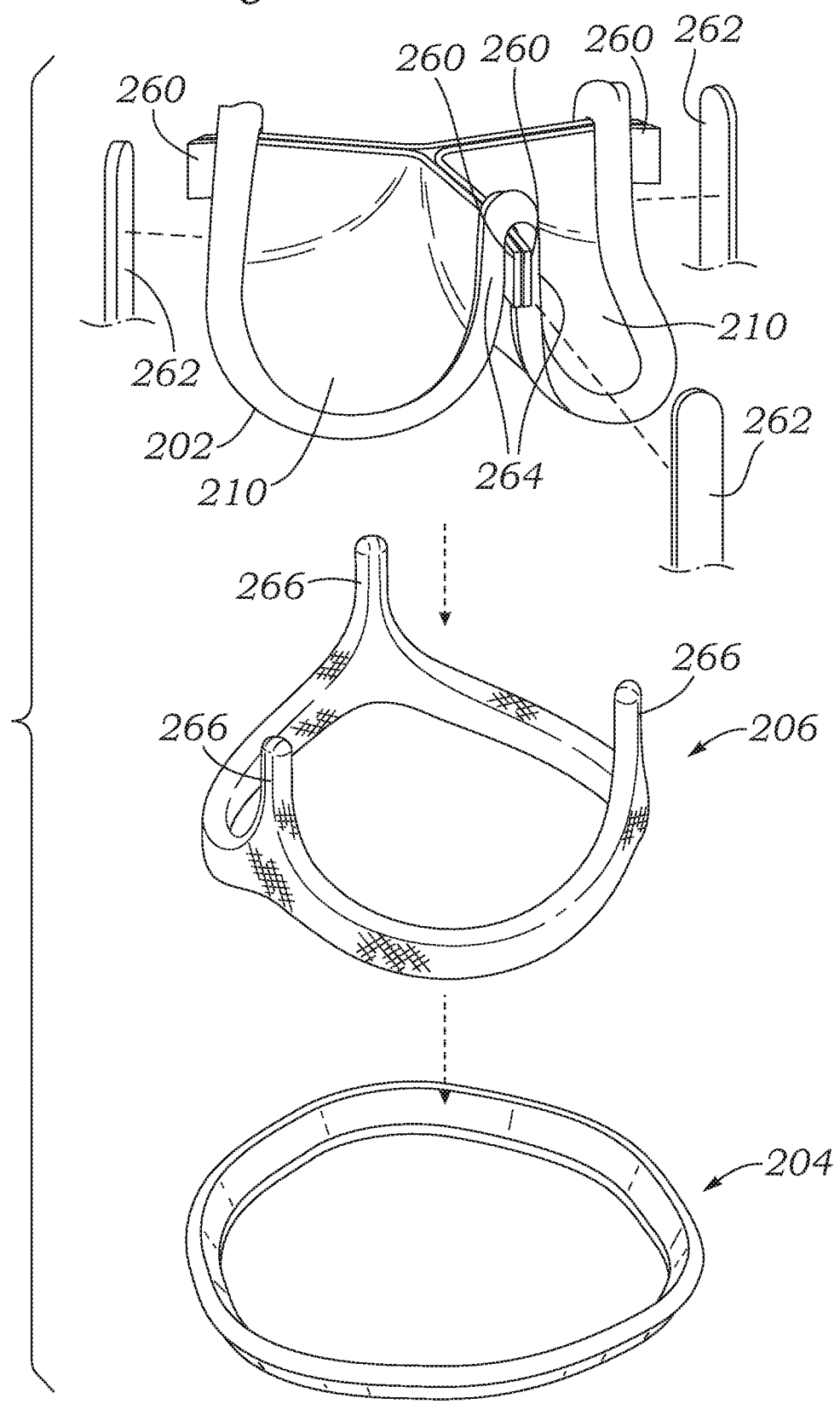
FIG. 16 is an exploded view of the valve of FIG. 7 showing the assembly of the wireform assembly, the stent assembly and the sewing ring assembly.
Figure 17:
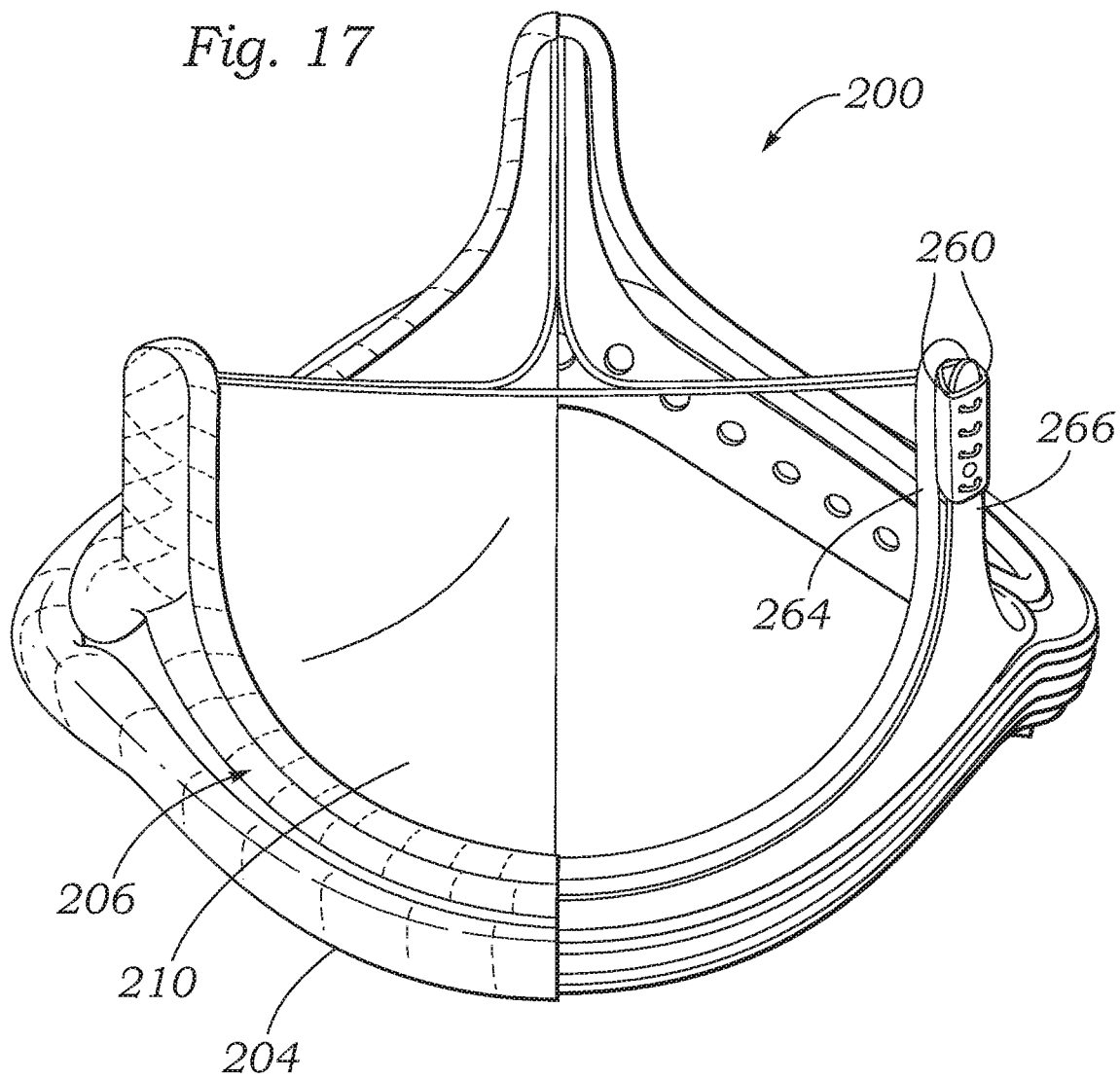
FIG. 17 is a perspective view of the heart valve of FIG. 7 shown partially in section.

Once the wireform assembly 202, sewing ring assembly 204, and stent assembly 206 are formed, these components can be assembled together with leaflets 210 to form the assembled valve. These components can be assembled in a conventional manner. As shown in FIG. 16, for example, three leaflets 210 can be positioned with the wireform assembly 202. Each leaflet 210 can include two tabs 260 positioned on opposing ends of the leaflet. Each respective tab 260 can be aligned with a tab 260 of an adjacent leaflet as shown. The lower edge of each leaflet extending between the tabs 260 can be sutured to the cloth covering 214 of the wireform assembly 202. Each pair of aligned tabs 260 can be inserted between adjacent upright extensions 264 of the wireform assembly 202. The tabs 260 can then be wrapped around a respective commissure support 266 of the stent assembly 206 (as best shown in FIG. 17). The tabs 260 can be sutured or otherwise coupled to each other and/or to the commissure post 266.

The wireform assembly 202 can be then be secured to an upper inner portion of the stent assembly 206 and the sewing ring assembly 204 can be secured to a lower outer portion of the stent assembly 206. The stent assembly 204 can matingly engage a corresponding contour of the wireform assembly. Thus, the commissure posts 266 and the cusp portions extending between the commissure posts can be sized and shaped so as to correspond to the curvature of the wireform assembly. The wireform assembly 202 can be secured to the stent assembly 206 via sutures extending through the cloth covering of the wireform assembly and the apertures in the inner support 240 and outer band 242 (FIG. 13) of the stent assembly. The sewing ring assembly 204 can be secured to the stent assembly via sutures extending through the sewing ring assembly and the apertures in the inner support 240 and outer band 242 (FIG. 13) of the stent assembly. Cloth covers 262 (FIG. 16) can be positioned over the exposed portions of the tabs 260 of the leaflets, and secured in place with sutures. The covers 262 can be formed from any biocompatible fabric or polymer.

Figure 18:
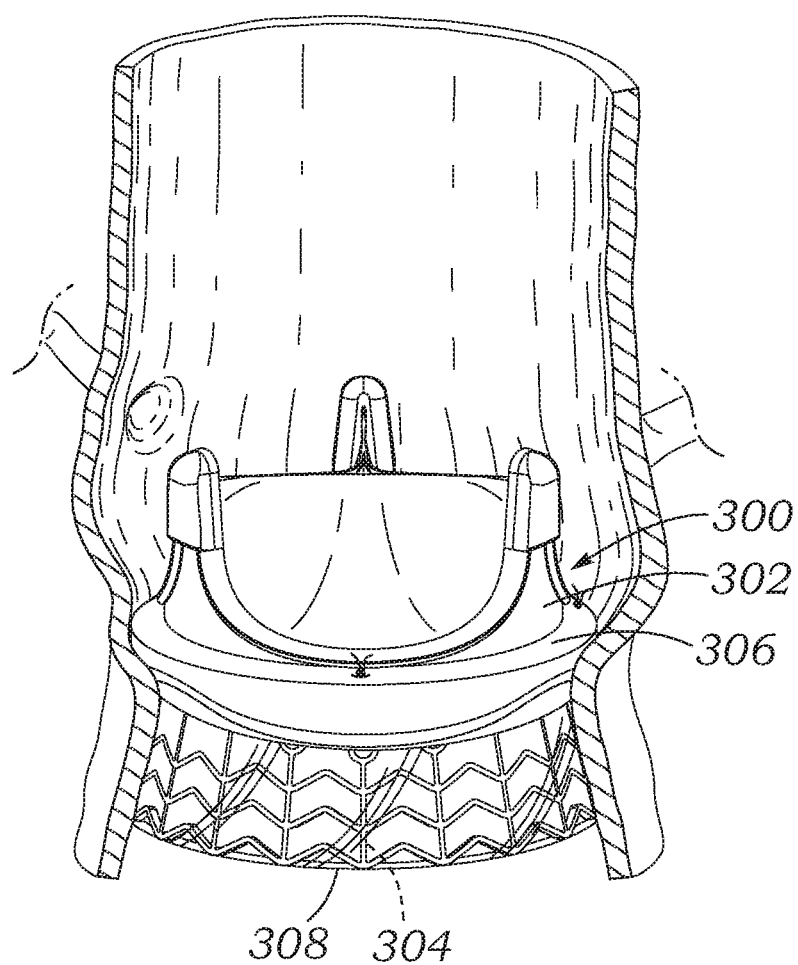
FIG. 18 is a perspective view of a heart valve, according to another embodiment.

FIG. 18 shows an embodiment of a heart valve 300, according to another embodiment. The heart valve can be implanted in the heart (e.g., in the aortic annulus, as shown in FIG. 18) using conventional surgical techniques or a minimally-invasive technique. The heart valve 300 includes a valve component 302 and an expandable frame component 304. The valve component 302 can be a conventional surgical valve having a sewing ring 306. The frame component 304 can be secured to the sewing ring using any of various connection techniques, such as suturing. In this embodiment, the frame component 304 can be deployed within a native heart valve annulus similar to a conventional transcatheter valve and therefore serves as an anchor for the valve component. Similar valves comprised of a surgical valve combined with an expandable frame and methods for implanting such valves are disclosed in U.S. Pat. No. 8,308,798 and U.S. Patent Publication No. 2012/0065729, which are incorporated herein by reference.

The valve 300 desirably comprises inner and outer layers 308 covering the inside and outside of the metal frame component 304. The layers 308 can be formed from tubular ePTFE layers utilizing the techniques described above for securing encapsulating layers 84, 86 around frame 52. However, the valve 300 in the illustrated embodiment does not include a separate cloth layer covering the frame component 304, which in some applications may be needed to reinforce the ePTFE layers where they undergo significant stress from cyclic loading of the valve. As shown in FIG. 18, the frame component 304 functions primarily to anchor the valve within the native annulus. The ePTFE layers on the frame component facilitate ingrowth of tissue and provide perivalvular sealing below the sewing ring 306. Once implanted, most of the stress caused by cyclic loading of the valve is born by the valve component 302 and little, if any, cyclic loading is experienced by the frame component 304. As such, the ePTFE layers 308 can provide adequate perivalvular sealing without a separate fabric layer reinforcing the ePTFE layers.

In alternative embodiments, the valve 300 can include a fabric layer (not shown) covering the inside and/or outside of the frame component 304. The fabric layer can be secured to the frame component 304 using the ePTFE layers as described herein.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for making an implantable prosthetic heart valve, comprising:
    forming a subassembly of the prosthetic heart valve comprising a radially collapsible and expandable tubular frame, the frame having an inlet end and outlet end, the frame comprising a plurality of connected struts defining cells and openings therebetween, and an annular fabric skirt positioned adjacent the frame;
    forming a first tubular covering member on a mandrel by a process of electrospinning;
    placing the subassembly over the first tubular covering member on the mandrel so that the first tubular covering member at least partly extends within the subassembly;
    forming a second tubular covering member over the subassembly on the first tubular covering member on the mandrel by a process of electrospinning so that the second tubular covering member at least partly covers the subassembly and is coextensive with the first tubular covering member;
    applying pressure to force the second tubular covering member and the first tubular covering member into contact with each other;
    heating the first and second tubular covering members so that they fuse together to form a monolithic covering that at least partially encapsulates the subassembly and thereby secures the fabric skirt to the annular frame; and
    suturing valvular leaflets to the monolithic covering and the subassembly, the leaflets being configured to permit blood flow in a first direction through the heart valve and block blood flow through the heart valve in a second direction, opposite the first direction.

2. The method of claim 1, wherein the first and second tubular covering members are non-absorbable and have a porous microstructure that promotes ingrowth of surrounding tissue to assist in securing the prosthetic heart valve in a body lumen.

3. The method of claim 2, wherein the first and second tubular covering members comprise ePTFE or UHMWPE.

4. The method of claim 1, wherein the fabric skirt is completely encapsulated by the covering formed by the first and second tubular covering members.

5. The method of claim 1, wherein the fabric skirt is disposed on the outside of the frame.

6. The method of claim 1, wherein the fabric skirt is disposed on the inside of the frame.

7. The method of claim 6, wherein the fabric skirt is also disposed on the outside of the frame.

8. The method of claim 1, further including removing material from the monolithic covering at locations that correspond to openings in the frame that are not covered by the fabric skirt.

9. The method of claim 8, wherein the step of removing material is done by laser cutting the material.

10. The method of claim 1, wherein an inflow end of the fabric skirt is aligned with an inflow end of the frame and a portion of the frame between an outflow end of the skirt and an outflow end of the frame is not covered by the inner and outer tubular covering members.

11. The method of claim 1, wherein the radially collapsible and expandable tubular frame is formed of a material that is plastically expandable.

12. The method of claim 11, wherein the annular fabric skirt is positioned around the frame, and the skirt is positioned on the frame by first partially crimping the frame to a diameter smaller than a diameter of the skirt, and then the skirt is placed over the partially crimped frame and the frame is expanded back to its functional size which applies at least some outward radial pressure against the skirt to assist in retaining the skirt on the frame.

13. The method of claim 1, wherein the radially collapsible and expandable tubular frame is formed of a material that is self-expandable.

14. The method of claim 1, wherein the step of suturing valvular leaflets to the monolithic covering includes securing a reinforcing strip to inner surfaces of lower edges of each of the leaflets, sandwiching the lower edges between the reinforcing strips and the skirt and suturing the lower edges of the leaflets to the skirt.

15. The method of claim 1, wherein the annular fabric skirt is positioned around the frame, and further including, after the step of placing the subassembly over the first covering member on the mandrel, wrapping layers of PTFE tape around opposite ends of the skirt and the frame to temporarily secure the location and placement of the skirt on the frame.

16. The method of claim 1, wherein the step of applying pressure to force the second tubular covering member and the first tubular covering member into contact with each other comprises tightly wrapping a PTFE tape around the entire outer surface of the assembly on the mandrel to apply pressure to the assembly.

17. The method of claim 1, wherein the skirt is a PET cloth and the first and second tubular covering members comprise ePTFE.

18. The method of claim 17, wherein the leaflets are made of bovine pericardium.

19. The method of claim 18, wherein the frame is formed of Nitinol.

20. The method of claim 18, wherein the frame is formed of a nickel-cobalt-chromium-molybdenum alloy.

* * * * *